United States Patent [19]

Treat

[11] Patent Number: 4,493,320

[45] Date of Patent: Jan. 15, 1985

[54] BIPOLAR ELECTROCAUTERY SURGICAL SNARE

[76] Inventor: Michael R. Treat, 792 Columbus Ave., Apt. 4E, New York, N.Y. 10025

[21] Appl. No.: 364,977

[22] Filed: Apr. 2, 1982

[51] Int. Cl.³ .............................................. A61B 17/39
[52] U.S. Cl. .................................................. 128/303.15
[58] Field of Search ..................... 128/303.13–303.17, 128/784, 785, 786, 320

[56] References Cited

U.S. PATENT DOCUMENTS

| | | | |
|---|---|---|---|
| 2,033,397 | 3/1936 | Richman | 128/784 X |
| 2,484,059 | 10/1949 | Wallace | 128/303.15 |
| 3,805,791 | 4/1974 | Seuberth et al. | 128/303.14 |
| 3,903,892 | 9/1975 | Komiya | 128/303.15 |
| 3,910,279 | 10/1975 | Okada et al. | 128/303.15 |
| 3,939,839 | 2/1976 | Curtiss | 128/303.15 |
| 3,955,578 | 5/1976 | Chamness et al. | 128/303.15 |
| 4,016,881 | 4/1977 | Rioux et al. | 128/303.17 |
| 4,202,338 | 5/1980 | Bitrolf | 128/303.15 |
| 4,256,113 | 3/1981 | Chamness | 128/303.14 |
| 4,311,143 | 1/1982 | Komiya | 128/303.15 |
| 4,311,145 | 1/1982 | Esty et al. | 128/303.17 |
| 4,345,599 | 8/1982 | McCarrell | 128/303.16 X |

FOREIGN PATENT DOCUMENTS

| | | | |
|---|---|---|---|
| 2514501 | 10/1976 | Fed. Rep. of Germany | 128/303.17 |
| 2275226 | 1/1976 | France | 128/303.17 |

Primary Examiner—Lee S. Cohen
Attorney, Agent, or Firm—Hedman, Gibson, Costigan & Hoare

[57] ABSTRACT

A bipolar electrocautery surgical snare is described capable of performing the endoscopic removal of growths within a body cavity with improved precision and accuracy. The bipolar surgical snare comprises an electrically insulating elongated double lumen tubular member, a pair of flexible electrically conductive snare wires extending through the respective lumina of the tubular member and from each end thereof, an electrically insulating connector means for mechanically uniting but electrically insulating one end of each of the snare wires to form a surgical loop extending from one end of the tubular member; and attachment for electrically connecting the opposed ends of said snare wires to a high frequency electrocautery current source.

7 Claims, 7 Drawing Figures

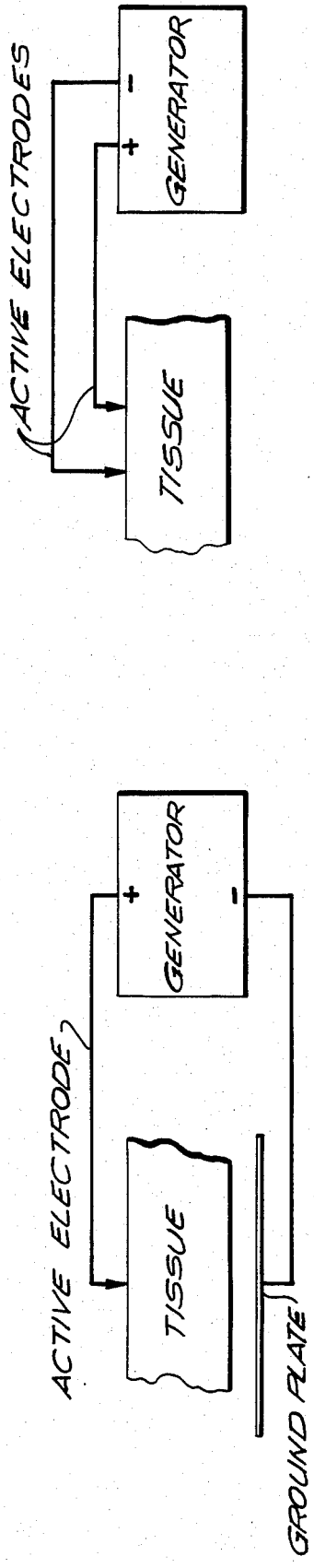
FIG.2
FIG.1
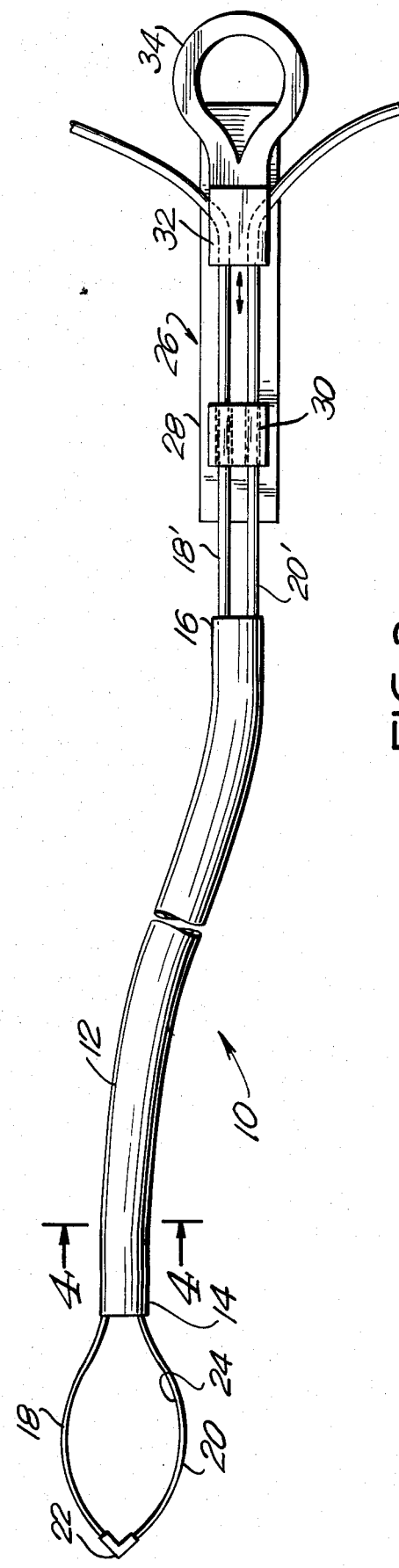
FIG.3

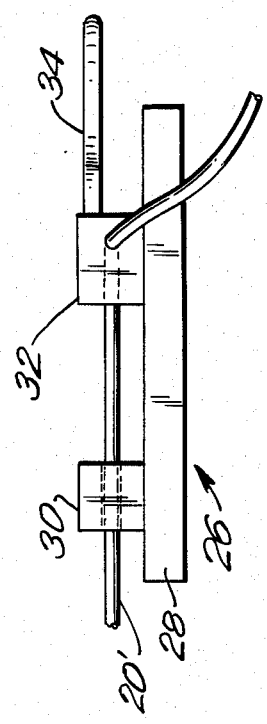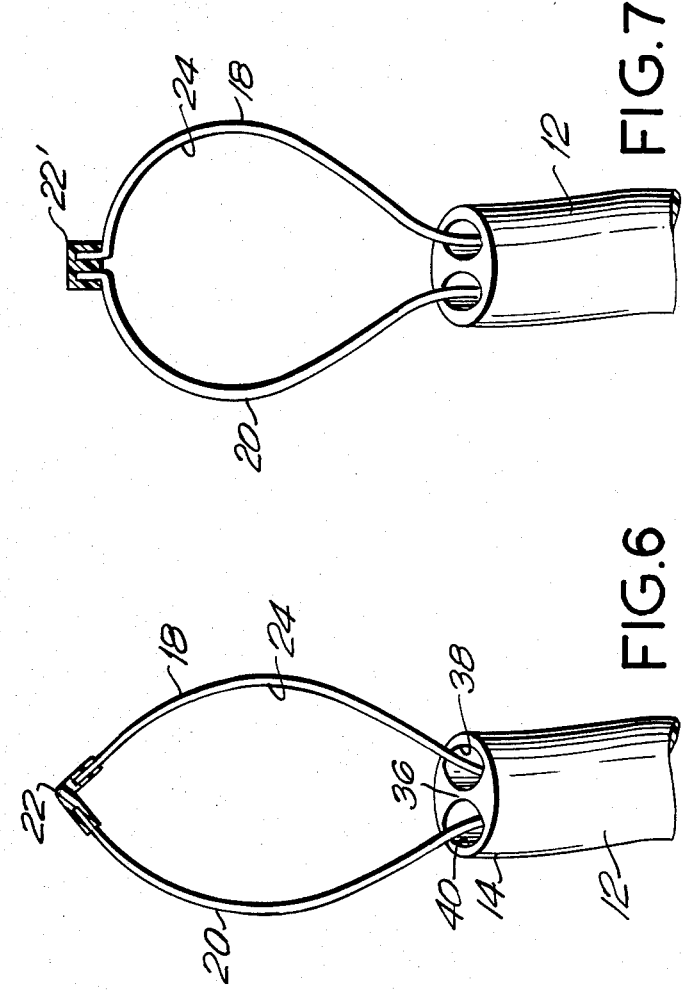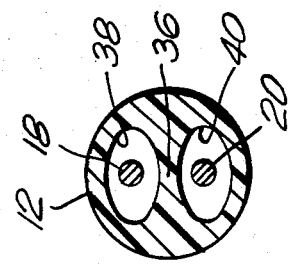

BIPOLAR ELECTROCAUTERY SURGICAL SNARE

BACKGROUND OF THE INVENTION

The present invention relates to endoscopic surgical instruments. More particularly, it relates to a new and improved bipolar electrocautery snare for use with such instruments.

Endoscopic surgical instruments such as bronchoscopes, colonoscopes, gastroscopes, sigmoidoscopes, and the like, are widely used at present by the medical profession. An endoscope generally comprises a tube or cannula containing a variety of instruments. The endoscope is inserted through an orifice into a body organ such as the lungs, bladder or prostate, or a body cavity, such as the intestines. More particularly, endoscopes are usually provided with an optical observation system which includes for example a lamp, an objective lens, an image guide formed of a flexible bundle of optical fibers and an eyepiece, which enables a surgeon to visually examine the internal environment surrounding the inserted end of the endoscope. Fluid conveying tubes are also provided within the endoscope for delivery of irrigation fluid to and withdrawal of blood and other fluids from the surgical area located adjacent to the end of the tube. An instrument channel is provided to slidably receive a surgical instrument, such as a cutting surgical electrode in the form of a loop or snare. The surgical snare may be extended or withdrawn from the end of the endoscope and can be made to surround any undesirable growth within the body organ or cavity. The snare is electrically connected to a high frequency electric current source which when activated passes a high frequency current through the loop which cauterizes the tissue growth within its grasp.

The development of endoscopy has provided great improvements in the surgical arts. In bowel surgery for instance, the surgeon is now able to get a close up view of lesions or growths, to perform biopsies for testing, or remove growths entirely, without the need to perform a laparotomy. The patient may thereby forgo certain life-threatening risks, such as sepsis, associated with that particular surgical procedure.

Surgical electrocautery snares for use with endoscopes are described, for example in U.S. Pat. No. 2,484,059 and U.S. Pat. No. 3,995,578. Typically, and as described therein, the surgical snare is formed of a flexible resilient stainless steel wire which is specially shaped to form an expandable loop as it is extended from an electrically insulated sheath. As the snare is pulled back into its sheath, the diameter of the loop gradually decreases. The ends of the snare loop are electrically connected to a flexible conductive wire extending within the protective sheath which is in turn electrically connected to one terminal of a high frequency electrocautery frequency source. The patient is grounded or otherwise connected to the other terminal of the high frequency source. To resect a growth, such as a polyp or tumor extending from an otherwise healthy tissue wall, the snare is positioned around the base of the growth and tightened to gather the tissue at the point of attachment of growth to tissue wall.

With the snare in position, the high frequency current generator is activated causing the flow of electrocauterizing current to pass from the loop to the tissue at the point of contact and then through the patient's body to ground. The snare is tightened as the current is applied until complete removal of the growth is achieved. One advantage of this type of surgery is that it is relatively bloodless because the snare electrode cauterizes the tissue as it cuts through it. A serious shortcoming of such snares is that they are unipolar. Current must pass from the snare loop through the patient's body to ground and aberrant or stray return currents, not localized to the point of attachment of the growth have been observed. These aberrant return currents can cause burns and discomfort to the patient and unintentional cauterization of healthy tissue, all of which are extremely undesirable.

Although presently available unipolar snares are serviceable in experienced hands, situations frequently arise in which surgeons desire a greater degree of control over the extent of tissue being cauterized. In order to better illustrate the problem, a schematic drawing of the unipolar electrocautery procedure is provided in FIG. 1. As illustrated therein, current flows from the electrocautery current generator to an active electrode. The current then must propagate through the entire volume of tissue in order to return to the ground plate and back to the other terminal of the generator. A partial limitation of the extent of tissue cauterized is provided because the current density at the small active electrode is much greater than the current density at the large ground plate, even though the same total amount of current that leaves the active electrode must return through the ground plate. The localization, however, is imperfect and is often not as precise as desired.

Bipolar electrocautery is a well-recognized method for overcoming the limitations of unipolar electrocautery. As schematically depicted in FIG. 2, bipolar electrocautery involves the use of two active electrodes. In this bipolar procedure current travels from the generator to one active electrode and returns via the second active electrode. In this procedure the current path lies largely in the small volume of tissue around the two electrodes. Although some slight spreading of current effect may occur, the effective radius of cauterization is far less than with the unipolar method.

Bipolar electrocautery is of considerable benefit in area where close control of the amount of tissue being cauterized is essential. Hertofore it has found wide application in the field of neurosurgery. However, in endoscopic surgery it is also very important to have precise control over the amount of tissue being cauterized. More particularly, during endoscopic removal of growths in the intestines, precise control of the amount of cauterization would be helpful in minimizing the risk of perforation of the intestinal wall. This is especially true in the colon, where the incidence of growths requiring removal is quite high and for which the intestinal wall is quite thin.

It has generally been believed that if the advantages of bipolar electrocautery could be applied to endoscopic surgery, a substantial safety margin for these surgical procedures could be provided. However, a bipolar electrocautery surgical snare for use with endoscopes has remained unavailable.

Accordingly, it is an object of the subject invention to provide a new and improved electrosurgical snare which is bipolar.

It is another object of the subject invention to provide a bipolar surgical snare which permits endoscopic electrocauterization of growths within the body of a surgical patient with precision and accuracy.

It is a further object of the subject invention to provide a bipolar electrosurgical snare which allows for the endoscopic removal of growths with reduced or eliminated risk to both the patient and surgeon of injury from aberrant or stray return currents.

SUMMARY OF THE INVENTION

In accordance with these and many other objects, the new and improved bipolar electrocautery surgical snare of the subject invention comprises:

a unitary elongated double lumen tubular member formed of an electrically insulating material and having a distal end and a proximal end;

a pair of elongated, flexible, electrically conductive snare wires, each snare wire being disposed within one of the respective lumina within said tubular member and each said snare wire being of such length that each snare wire extends outwardly from both the distal end and proximal ends of said tubular member;

a connector means disposed at the distal end of each of said snare wires formed of an electrically insulating material, said connector means mechanically uniting, but electrically insulating said distal ends of said snare wires to form a surgical snare loop extending from the distal end of said tubular member;

means for electrically connecting the proximal ends of said snare wires to a bipolar electrocautery current source; and actuator means for sliding the snare wires inwardly and outwardly through the tubular member to respectively expand and contract the surgical loop.

The unitary double lumen member of the subject invention includes a septum or divider extending along its length which forms an electrically insulating barrier between the two snare wires. The tubular member may be inserted into an organ or body cavity either alone or within the instrument channel of an endoscope. The tubular member may be stiff or flexible depending upon the type of endoscope being used and may be formed of any electrically insulating plastic material.

In preferred embodiments the tubular member is formed from a poly(tetrafluoroethylene) (TEFLON) material. The snare wires are made of stainless spring steel. The connector means will generally be of a non-conductive plastic material having a high dielectric constant, such as TEFLON or polyethylene.

In use, the tubular member is inserted into a body cavity either alone or as an integral part of an endoscope. When the distal end of the tubular member is brought into position adjacent a growth to be resected, the snare wires are pushed inwardly through the tubular member to expand the surgical loop extending from the distal end. The surgical loop is positioned around the growth at the base thereof where the growth adjoins the wall of healthy tissue by manipulation of the endoscope or tubular member. The snare is then tightened by withdrawing or pulling the snare wires outwardly from the proximal end of the tubular member so that the snare strangulates the growth at its point of attachment. The high frequency electrocautery generator is turned on and electrocauterizing current flows from one snare wire making up one side of the surgical loop, through the grasped tissue to the snare wire comprising the other side of the loop. The current is thus uniformly directed from one side of the loop to the opposed side in a substantially planar fashion. Aberrant or stray return currents are effectively reduced or eliminated. This flow of current from one snare wire to the other, travelling in substantially only one plane, provides for a precise and accurate electrocauteral resection of lesions heretofore unattainable with presently available unipolar electrosurgical snares.

Other objects and advantages of the subject invention will become apparent from the following detailed description, taken in conjunction with the drawings in which:

BRIEF DESCRIPTION OF THE DRAWINGS

FIG. 1 is a schematic diagram of a unipolar electrocautery device.

FIG. 2 is a schematic diagram of a bipolar electrocautery device.

FIG. 3 is a top plan view of the new and improved bipolar electrocautery surgical snare of the subject invention.

FIG. 4 is an elevated cross sectional view of the new and improved bipolar electrocautery surgical snare of the subject invention taken along lines 4—4 from FIG. 3.

FIG. 5 is an elevated side view of the preferred actuator means of the new and improved bipolar electrocautery surgical snare of the subject invention.

FIG. 6 is a magnified elevational side view of the distal end of the new and improved bipolar electrocautery surgical snare of the subject invention.

FIG. 7 is a magnified elevational side view of an alternate embodiment of the distal end of the new and improved bipolar electrocautery surgical snare of the subject invention.

DETAILED DESCRIPTION OF THE PREFERRED EMBODIMENT

Referring to FIG. 3, the new and improved bipolar electrocautery surgical snare of the present invention, generally referred to by the numeral 10, is shown. In the preferred embodiment depicted therein, bipolar surgical snare 10 comprises an elongated tubular member 12 having a distal end 14 and a proximal end 16. A pair of independent snare wires 18 and 20, each extend through tubular member 12 and are of such a length that each extend outwardly from both distal end 14 and proximal end 16 of tubular member 12. A connector means 22 disposed at the distal ends of each snare wire 18 and 20, respectively, mechanically unites but electrically insulates the snare wires extending from distal end 14 of tubular member 12 in such manner as to form a surgical loop 24. The proximal ends of snare wires 18 and 20 extending from the proximal end 16 of tubular member 12 are preferably coated with an electrically insulating wire enamel shown as 18' and 20' respectively. Snare wires 18' and 20' extend from proximal end 16 and are ultimately connected to a high frequency electrocautery current source, labelled voltage source in FIG. 3, by any suitable electrically connecting means, such as an electrical jack or terminal-screw, and the like. An electrically insulated actuator means 26 is disposed intermediate proximal end 16 of tubular member 12 and the voltage source.

More particularly, actuator means 26 is generally formed of parts of molded plastic materials and includes an elongated base member 28, fixed abutment 30, and a slide block 32 and having a handle 34 affixed thereto. Slide block 32 is slidable along the longitudinal axis of base member 28 and this capability may be provided by any suitable means, such as tongue in groove, sliding tracks, or the like. The insulated proximal ends of snare wires 18' and 20' extend through fixed abutment 30 in slidable relation therewith, and in such manner that snare wires 18' and 20' are maintained in a spaced relationship therethrough. The snare wires extend from fixed abutment 30 and enter slide block 32 through its distal surface and pass therethrough in a spaced and curved fashion such that each of the snare wires exit from one of the opposed side walls of slide block 32, respectively, and from there extend to the electrocautery voltage source. Snare wires 18' and 20' are held in fixed relation to slide block 32 such that movement of slide block 32 is manually operative to slide the snare wires inwardly or outwardly through the tubular member to expand or retract surgical loop 24 from distal end 14. By manipulation of the endoscope or tubular member in conjunction with actuator means 26, the surgical loop 24 may be positioned around a growth to be resected.

In the preferred embodiment depicted in FIG. 3, tubular member 12 is flexible and may be used in a flexible type endoscope such as colonoscope. Tubular member 12 may be formed from an electrically insulating material and must have a structure which electrically insulates the snare wires from each other along its entire length. Preferably, tubular member 12 is of the double lumen type as shown in FIG. 4. As depicted therein tubular member 12 is of a unitary construction. The interior portion of the tubular member includes a septum or divider 36 extending along its length which divides the interior in such manner as to form a pair of discreet channels or passages 38 and 40. Snare wires 18 and 20 extend within the respective passages in slidable relation therewith and are thereby electrically insulated from each other along the entire length of the tubular member.

The electrically insulating connector means 22 disposed at the distal ends of the snare wires is, as has already been mentioned, formed of an electrically insulative material, for example a plastic material such as Teflon or polyethylene, or may be a ceramic, glass, or epoxy material. Referring to FIGS. 6 and 7 connector means 22 may preferably have a wide V-shape. The distal ends of each of the snare wires are imbedded in one of the respective legs of the V and so are mechanically united but remain electrically insulated. The angle formed between the two legs of the V causes the snare wires to expand outwardly away from each other thereby forming the surgical loop 24 as the snare wires are extended from the distal end of the tubular member by operation of actuator means 26.

In an alternate embodiment depicted in FIG. 7, connector means 22' has a different structure. As illustrated therein, connector means 22' is of a solid rectangular or circular shape. The distal ends of snare wires 18 and 20 are imbedded therein so that they extend within connector means 22' in a spaced parallel fashion. The space between the distal ends of the wires is filled with the electrically insulating material comprising the connector means so that again the distal ends of the snare wires are mechanically united but electrically insulated. In the alternate embodiment shown, the snare wires have been bent or crimped at the base of connector means 22' which causes the snare wires to flare outwardly to form the surgical loop upon extension from the tubular member.

The snare wires 18 and 20 are preferably made of stainless spring steel, although any electrical conductor such as silver or platinum wire may be used. Generally, the snare wires have a diameter of less than 1 mm but any thickness may be used so long as the snare wires are flexible and resilient. The length of the snare wires and length of the tubular member will vary in accordance with the type of endoscope used and is generally not critical to the invention.

In use, the surgical loop is made to surround the base of a polyp, tumor, or other undesirable growth and slide block 32 is slid rearwardly away from fixed abutment 30 thereby causing the snare wires to be withdrawn back into the tubular member. This in turn causes the diameter of the snare loop to decrease and strangle the tissue at the base of the growth. The voltage source is switched on by any suitable switch device, such as a foot pedal, thereby sending a pulse of electrocauterizing current from one terminal of the voltage source up through one snare wire, through the grasped tissue to the other snare wire, and back to the other terminal of the voltage source. The amount of tissue exposed to electrocauterizing current is thus kept at a minimum, being substantially limited to that tissue located between the snare wires of the surgical loop and in the same plane as the snare wires. The snare is tightened and another pulse is sent, which procedure is repeated until the growth has thoroughly been resected. A controlled precise and accurate bipolar electrocautery surgical snare for the endoscopic removal of growths within a surgical patient is thereby provided.

Although the subject invention has been described with reference to a preferred embodiment, it is apparent that modifications and changes may be made therein by those skilled in the art without departing from the scope and spirit of the present invention as defined by the appended claims.

What is claimed is:

1. A bipolar electrocautery surgical snare for endoscopic removal of growths within a body cavity, said snare comprising:
    a unitary elongated electrically insulating flexible double-lumen tubular member having a proximal end and a distal end;
    a pair of elongated flexible electrically conductive uninsulated snare wires, each snare wire disposed within one of the respective lumina within said tubular member in slidable relation therewith, said snare wires being of a length greater than said tubular member such that each snare wire extends from both the proximal and distal ends of said tubular member;
    an electrically insulating connector means disposed at the distal end of each of said snare wires; said connector means mechanically uniting but electrically insulating said distal ends of said snare wires to form a surgical snare loop extending from the distal end of said tubular member; and
    means for electrically connecting the proximal ends of said snare wires to a bipolar electrocautery current source; and
    actuator means for sliding the snare wires inwardly or outwardly through the tubular member to respectively expand or contract the surgical loop.

2. A bipolar electrocautery surgical snare as recited in claim 1 wherein said tubular member and said connector means are formed of an electrically insulating material selected from the group consisting of plastic, ceramic, glass and epoxy.

3. A bipolar electrocautery surgical snare as recited in claim 1 wherein said pair of snare wires are comprised of a metal selected from the group consisting of stainless steel, spring steel, platinum and silver.

4. A bipolar electrocautery surgical snare as recited in claim 1 wherein said actuator means comprises:
- an elongated base member;
- the proximal ends of said snare wires;
- a fixed abutment disposed at one end of the base member, said fixed abutment including a pair of spaced apertures therethrough slidably receiving the proximal ends of said snare wires; and
- a slide block slidably mounted to said base member and slidable along the longitudinal axis thereof, said slide block including a pair of spaced and oppositely curved passages extending therethrough from the distal face thereof to one of the opposed side walls of the slide block, each of said passages fixedly receiving one of the respective snare wires therethrough, said slide block further including a handle member extending from the proximal face thereof, whereby movement of said slide block is manually operative to slide said snare wires through said tubular member to expand or retract said surgical loop extending from the distal end of the tubular member.

5. A bipolar electrocautery surgical snare as recited in claim 1 wherein said tubular member and said electrically insulating connector means are formed of polytetrafluoroethylene or polyethylene.

6. A bipolar electrocautery surgical snare as recited in claim 1 wherein said connector means is a V-shaped piece of molded plastic with each of the distal ends of said snare wires extending within one of the respective legs of the V, such that when the snare wires are pushed inwardly through the tubular member, the snare wires will flare outwardly from the distal end of the tubular member to form a surgical snare loop.

7. A bipolar electrocautery snare as recited in claim 1 wherein said connector means is formed of a solid piece of plastic material with the distal ends of the snare wires extending therein in spaced parallel fashion, and said distal ends of the snare wires being crimped outwardly at the point at which they extend from said connector means in such manner as to cause the snare wires to flare outwardly from the distal end of the tubular member to form a surgical snare loop as the snare wires are pushed inwardly through the tubular member.

* * * * *